United States Patent
Saikou

(10) Patent No.: US 11,969,143 B2
(45) Date of Patent: Apr. 30, 2024

(54) TARGET PART IDENTIFICATION AMONG HUMAN-BODY INTERNAL IMAGES

(71) Applicant: NEC Corporation, Tokyo (JP)

(72) Inventor: Masahiro Saikou, Tokyo (JP)

(73) Assignee: NEC CORPORATION, Tokyo (JP)

( * ) Notice: Subject to any disclaimer, the term of this patent is extended or adjusted under 35 U.S.C. 154(b) by 626 days.

(21) Appl. No.: 17/258,296

(22) PCT Filed: Jul. 9, 2018

(86) PCT No.: PCT/JP2018/025871
§ 371 (c)(1),
(2) Date: Jan. 6, 2021

(87) PCT Pub. No.: WO2020/012530
PCT Pub. Date: Jan. 16, 2020

(65) Prior Publication Data
US 2021/0267544 A1    Sep. 2, 2021

(51) Int. Cl.
*A61B 1/00* (2006.01)
*A61B 5/00* (2006.01)
(Continued)

(52) U.S. Cl.
CPC .. *A61B 1/000094* (2022.02); *A61B 1/000096* (2022.02); *A61B 5/4887* (2013.01);
(Continued)

(58) Field of Classification Search
CPC ........ A61B 1/000094; A61B 1/000096; A61B 5/4887; A61B 5/7221; A61B 34/10;
(Continued)

(56) References Cited

U.S. PATENT DOCUMENTS

2002/0097320 A1    7/2002  Zalis
2012/0230583 A1    9/2012  Inoshita
(Continued)

FOREIGN PATENT DOCUMENTS

JP    2004-500213 A    1/2004
JP    2009-50321 A     3/2009
(Continued)

OTHER PUBLICATIONS

Japanese Office Action for JP Application No. 2020-529855 dated Aug. 24, 2021 with English Translation.
(Continued)

*Primary Examiner* — Casey L Kretzer
(74) *Attorney, Agent, or Firm* — Sughrue Mion, PLLC

(57) ABSTRACT

Provided are a surgery assistance apparatus, a surgery assistance method, and a computer readable recording medium that includes a surgery assistance program recorded thereon that improve the accuracy of endoscopic surgery by identifying a target part image. A surgery assistance apparatus 1 includes a feature amount calculation unit 2 that calculates, from a human-body internal image captured using an endoscope, a feature amount of a target part image corresponding to a target part, a similarity degree calculation unit 3 that calculates a similarity degree of the features amount between different human-body internal images, and an identification unit 4 that identifies the target part image in each of the different human-body internal images if the similarity degree is greater than or equal to a predetermined value.

11 Claims, 10 Drawing Sheets

(51) Int. Cl.
 *A61B 34/10* (2016.01)
 *G06T 7/73* (2017.01)
(52) U.S. Cl.
 CPC ............ *A61B 5/7221* (2013.01); *A61B 34/10* (2016.02); *G06T 7/73* (2017.01); *A61B 2034/107* (2016.02); *G06T 2207/10048* (2013.01); *G06T 2207/10068* (2013.01); *G06T 2207/30096* (2013.01)
(58) Field of Classification Search
 CPC ................ A61B 2034/107; G06T 7/73; G06T 2207/10048; G06T 2207/10068; G06T 2207/30096
 See application file for complete search history.

(56) References Cited

U.S. PATENT DOCUMENTS

| | | |
|---|---|---|
| 2014/0187920 A1 | 7/2014 | Millett et al. |
| 2016/0350912 A1 | 12/2016 | Koide et al. |
| 2017/0004625 A1 | 1/2017 | Kamiyama et al. |
| 2018/0279862 A1* | 10/2018 | Wade ..................... A61B 34/25 |
| 2020/0184645 A1* | 6/2020 | Kamon ............ A61B 1/000094 |

FOREIGN PATENT DOCUMENTS

| | | |
|---|---|---|
| JP | 2012-11137 A | 1/2012 |
| JP | 2011/061905 A1 | 4/2013 |
| JP | 2015-181594 A | 10/2015 |
| JP | 2016-507280 A | 3/2016 |
| JP | 2017-213058 A | 12/2017 |
| WO | 2015/118850 A1 | 8/2015 |

OTHER PUBLICATIONS

English translation of Written opinion for PCT Application No. JP2018/025871, dated Sep. 25, 2018.
International Search Report for PCT Application No. PCT/JP2018/025871, dated Sep. 25, 2018.

* cited by examiner

Fig.5
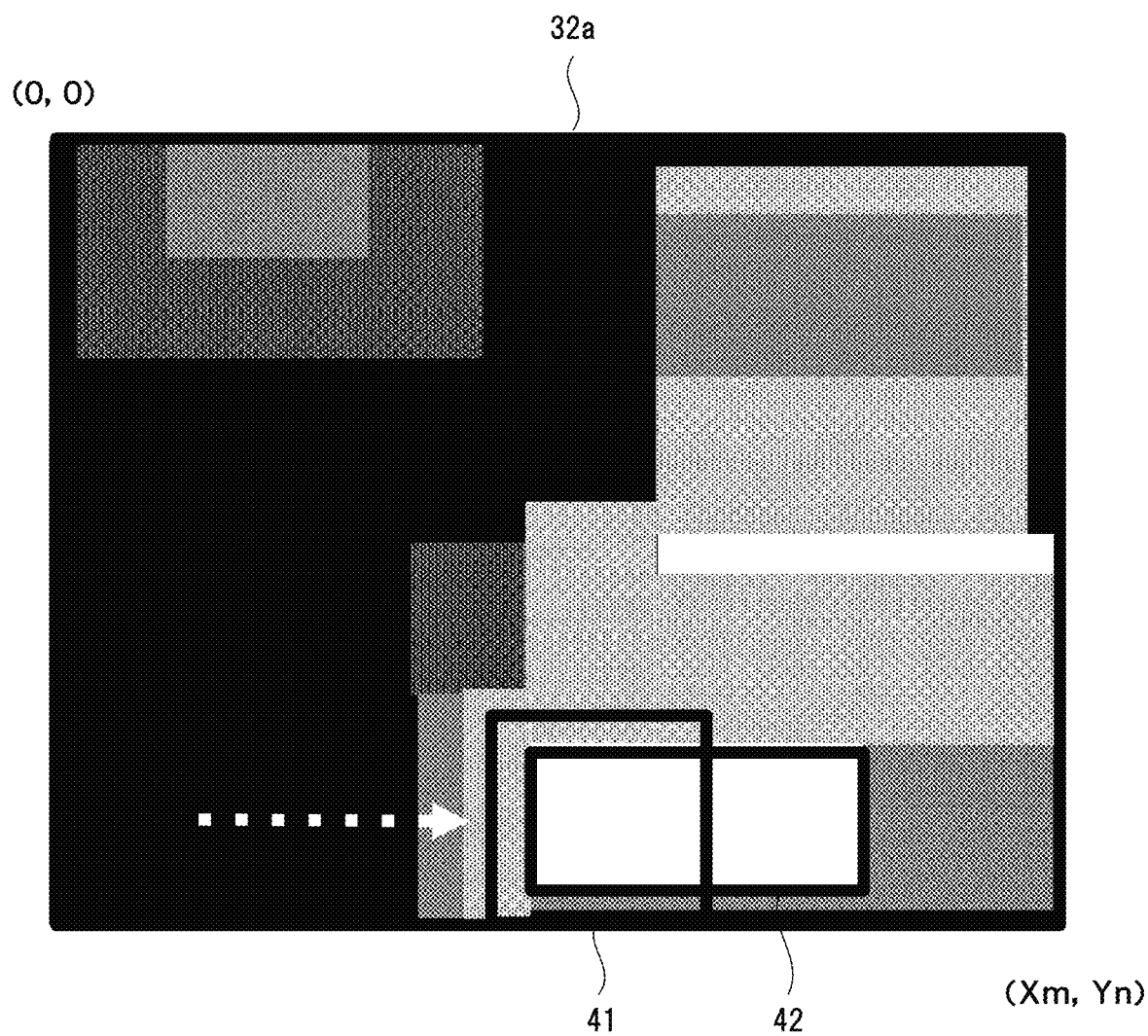
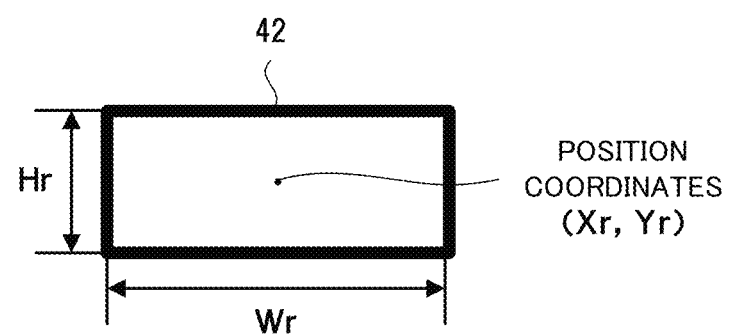

| HUMAN-BODY INTERNAL IMAGE | 31a |
|---|---|
| FEATURE EXTRACTION INFORMATION | fa = (f1a, f2a, ⋯ fna) |
| DETECTION RESULT INFORMATION | r1a = (X1a, Y1a, W1a, H1a, conf1a) |
| | r2a = (X2a, Y2a, W2a, H2a, conf2a) |
| | r3a = (X3a, Y3a, W3a, H3a, conf3a) |
| | r4a = (X4a, Y4a, W4a, H4a, conf4a) |
| HEATMAP INFORMATION | ha = (h1a, h2a, ⋯ hna) |

61b

| HUMAN-BODY INTERNAL IMAGE | 31b |
|---|---|
| FEATURE EXTRACTION INFORMATION | fb = (f1b, f2b, ⋯ fnb) |
| DETECTION RESULT INFORMATION | r1b = (X1b, Y1b, W1b, H1b, conf1b) |
| | r2b = (X2b, Y2b, W2b, H2b, conf2b) |
| | r3b = (X3b, Y3b, W3b, H3b, conf3b) |
| | r4b = (X4b, Y4b, W4b, H4b, conf4b) |
| HEATMAP INFORMATION | hb = (h1b, h2b, ⋯ hnb) |

61c

| HUMAN-BODY INTERNAL IMAGE | 31c |
|---|---|
| FEATURE EXTRACTION INFORMATION | fc = (f1c, f2c, ⋯ fnc) |
| DETECTION RESULT INFORMATION | r1c = (X1c, Y1c, W1c, H1c, conf1c) |
| | r2c = (X2c, Y2c, W2c, H2c, conf2c) |
| | r3c = (X3c, Y3c, W3c, H3c, conf3c) |
| | r4c = (X4c, Y4c, W4c, H4c, conf4c) |
| HEATMAP INFORMATION | hc = (h1c, h2c, ⋯ hnc) |

TARGET PART IDENTIFICATION AMONG HUMAN-BODY INTERNAL IMAGES

This application is a National Stage Entry of PCT/JP2018/025871 filed on Jul. 9, 2018, the contents of all of which are incorporated herein by reference, in their entirety.

TECHNICAL FIELD

The present invention relates to a surgery assistance apparatus and a surgery assistance method for assisting endoscopic surgery, and further relates to a computer readable recording medium that includes a program for realizing the surgery assistance apparatus and the surgery assistance method recorded thereon.

BACKGROUND ART

A surgery assistance apparatus that extracts a target part image corresponding to a target part from an image obtained by capturing an image of the inside of a human body using an endoscope, and that uses the extracted target part image to assist an observer during surgery is known. Such an apparatus improves the accuracy of surgery by capturing an image of the inside of a colon, etc., using an endoscope, detecting a tumor that is likely to become cancerous from the captured image, and providing a notification to the observer, for example.

As a related technique, Patent Document 1 discloses an apparatus that extracts an affected-part image (target part image) corresponding to an affected part (target part) from an image obtained by capturing an image of the inside of a human body using an endoscope, and identifies the pathological type of the affected part on the basis of a result of feature amount matching processing between the extracted affected-part image and learning images.

LIST OF RELATED ART DOCUMENTS

Patent Document

Patent Document 1: International Publication No. 2015/118850

SUMMARY OF INVENTION

Technical Problems

However, the target part image cannot be tracked even if the above-described surgery assistance apparatus or the apparatus disclosed in Patent Document 1 is used. Furthermore, in the case where surgery is performed using an endoscope, it is difficult to track the target part image even if a conventional tracking technique (such as optical flow, for example) is used.

In the case where surgery is performed using an endoscope, movement of the target part image out of the frame, changes in the target part image brought about by the image-capturing distance, angle, etc., between the image-capturing unit of the endoscope and the target part changing as the endoscope is inserted and extracted, etc., make it difficult to track the target part image, for example.

It is also difficult to track the movement of the target part image because the target part is frequently concealed by parts of the human body other than the target part (for example, concealment of the target by intestinal folds, intestinal mucus, etc.) or by water ejected from the endoscope, etc.

Furthermore, it is difficult to track the target part image on the basis of shape or color because the internal parts of the human body and the target part are non-rigid objects (objects without definite shapes).

An example object of the present invention is to provide a surgery assistance apparatus, a surgery assistance method, and a computer readable recording medium that includes a surgery assistance program recorded thereon that improve the accuracy of endoscopic surgery by identifying a target part image.

Solution the Problems

In order to achieve the above-described object, a surgery assistance apparatus according to an example aspect of the present invention includes:
 a feature amount calculation unit configured to calculate, from a human-body internal image captured using an endoscope, a feature amount of a target part image corresponding to a target part;
 a similarity degree calculation unit configured to calculate a similarity degree of the feature amount between different ones of the human-body internal images; and
 an identification unit configured to identify the target part image in each of the different human-body internal images if the similarity degree is greater than or equal to a predetermined value.

In addition, in order to achieve the above-described object, a surgery assistance method according to an example aspect of the present invention includes:
 (a) a step of calculating, from a human-body internal image captured using an endoscope, a feature amount of a target part image corresponding to a target part;
 (b) a step of calculating a similarity degree of the feature amount between different ones of the human-body internal images; and
 (c) a step of identifying the target part image in each of the different human-body internal images if the similarity degree is greater than or equal to a predetermined value.

Furthermore, in order to achieve the above-described object, a computer readable recording medium that includes a surgery assistance program recorded thereon according to an example aspect of the present invention causes the following steps to be carried out:
 (a) a step of calculating, from a human-body internal image captured using an endoscope, a feature amount of a target part image corresponding to a target part;
 (b) a step of calculating a similarity degree of the feature amount between different ones of the human-body internal images; and
 (c) a step of identifying the target part image in each of the different human-body internal images if the similarity degree is greater than or equal to a predetermined value.

Advantageous Effects of the Invention

As described above, according to the present invention, the accuracy of endoscopic surgery can be improved by identifying a target part image.

BRIEF DESCRIPTION OF THE DRAWINGS

FIG. 5 is a diagram for describing the calculation of the detection result information.

FIG. 7 is a diagram illustrating one example of a data structure of feature amounts.

EXAMPLE EMBODIMENT

Example Embodiment

In the following, an example embodiment of the present invention will be described with reference to FIGS. 1 to 10.

[Apparatus Configuration]

Figure 1:
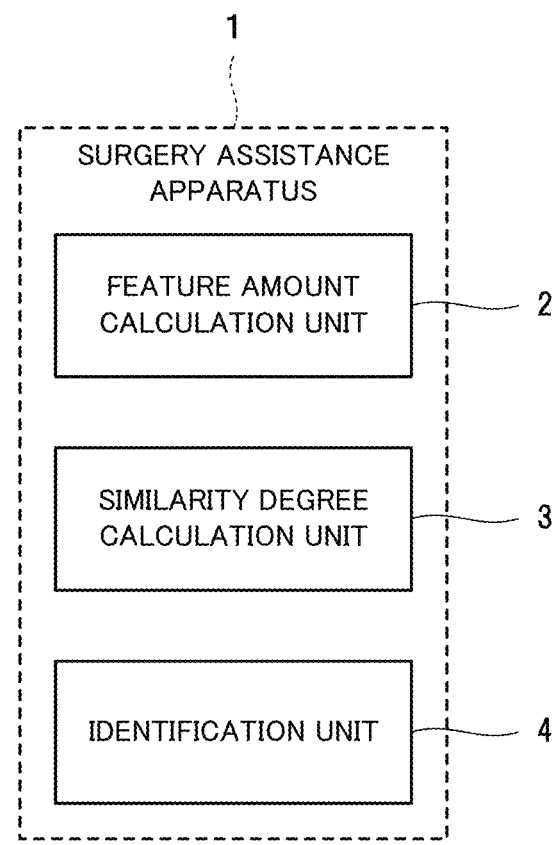
FIG. 1 is a diagram illustrating one example of a surgery assistance apparatus.

First, a configuration of a surgery assistance apparatus in the present example embodiment will be described with reference to FIG. 1. FIG. 1 is a diagram illustrating one example of the surgery assistance apparatus.

A surgery assistance apparatus 1 in the present example embodiment, which is illustrated in FIG. 1, is an apparatus for improving the accuracy of endoscopic surgery by using image processing and identifying a target part image. As illustrated in FIG. 1, the surgery assistance apparatus 1 includes a feature amount calculation unit 2, a similarity degree calculation unit 3, and an identification unit 4.

Of these units, the feature amount calculation unit 2 calculates, from a human-body internal image captured using an endoscope, a feature amount of a target part image corresponding to a target part. The similarity degree calculation unit 3 calculates a similarity degree of the feature amount between different ones of the human-body internal images. The identification unit 4 identifies the target part image in each of the different human-body internal images if the similarity degree is greater than or equal to a predetermined value.

In such a manner, in the present example embodiment, a target part image in different human-body internal images captured using an endoscope is identified if a similarity degree of a feature amount between the different human-body internal images is greater than or equal to a predetermined value. Thus, the accuracy of endoscopic surgery can be improved because a target part image can be tracked.

Specifically, an observer conventionally visually tracks a target part image, and thus there are cases where the observer cannot refind a target part image if the observer loses track of the target part image. In such cases, there is a risk of a target part which is likely to become cancerous and need surgery, etc., of being overlooked. However, because a target part image can be identified using the surgery assistance apparatus in the present example embodiment, cases where a target part is overlooked can be reduced, regardless of the observer's skill and the like, and thus the accuracy of surgery can be improved.

Cases where the observer loses track of a target part image that is captured using an endoscope can be reduced because a target part image can be identified even if the target part image moves out of the frame or the target part image undergoes changes (a change in the size of the target part, a change in the image-capturing range, rotation of the image, etc.) as the endoscope is inserted and extracted, for example. Accordingly, the accuracy of endoscopic surgery can be improved.

Also, cases where the observer loses track of a target part image can be reduced because a target part image can be identified even if the target part is frequently concealed by parts of the human body other than the target part (for example, concealment of the target by intestinal folds, intestinal mucus, etc.) or by water ejected from the endoscope, etc. Accordingly, the accuracy of endoscopic surgery can be improved.

Furthermore, cases where the observer loses track of a target part image can be reduced because a target part image can be identified even in the case of non-rigid objects (objects without definite shapes) such as internal parts of the human body and the target part. Accordingly, the accuracy of endoscopic surgery can be improved.

[System Configuration]

Figure 2:
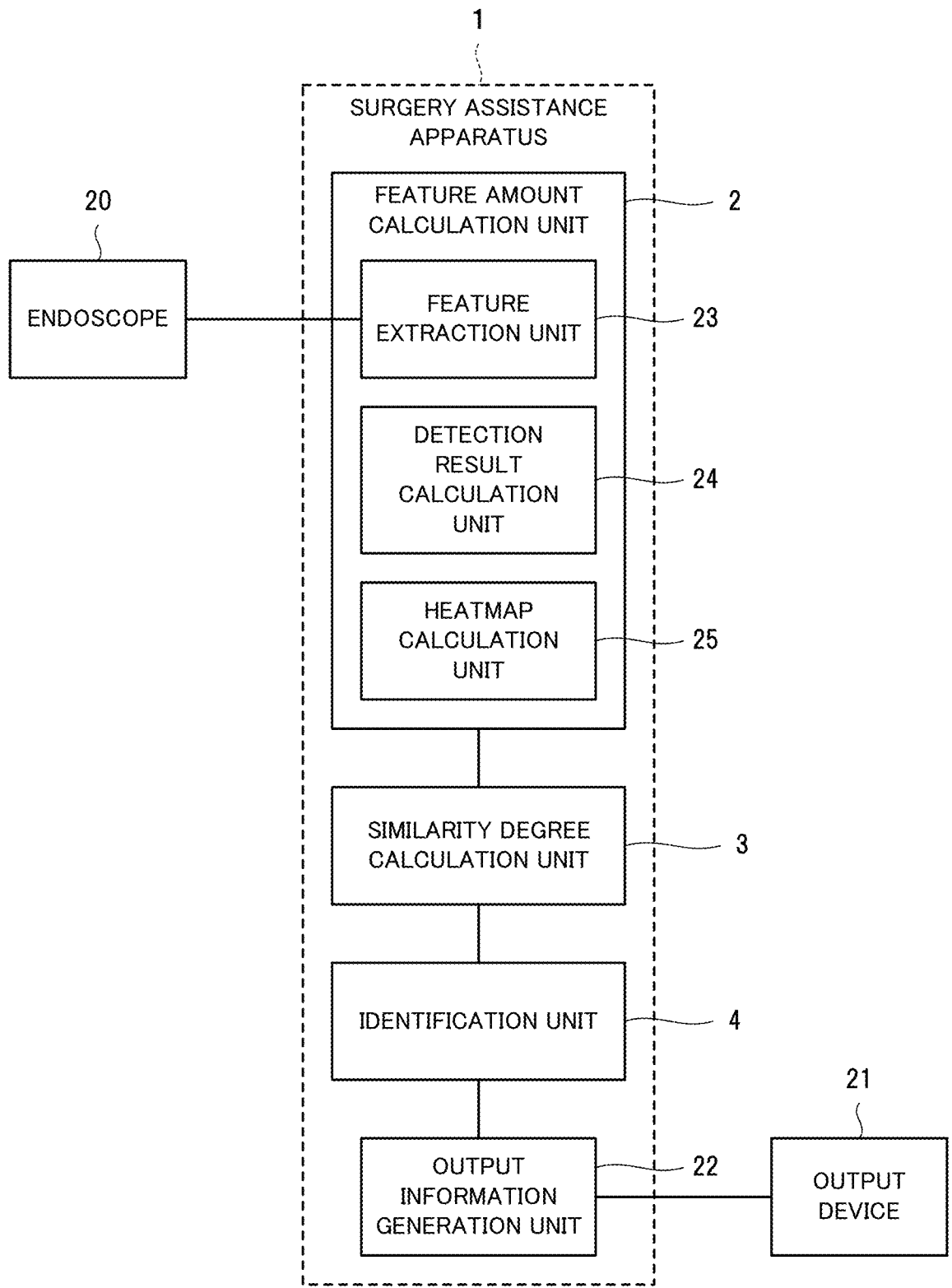
FIG. 2 is a diagram illustrating one example of the surgery assistance apparatus and a system including the surgery assistance apparatus.

Next, the configuration of the surgery assistance apparatus 1 in the present example embodiment will be specifically described with reference to FIG. 2. FIG. 2 is a diagram illustrating one example of the surgery assistance apparatus and a system including the surgery assistance apparatus.

As illustrated in FIG. 2, the system in the present example embodiment includes the surgery assistance apparatus 1 for executing image processing, an endoscope 20, and an output device 21. The surgery assistance apparatus 1 includes an output information generation unit 22 in addition to the feature amount calculation unit 2, the similarity degree calculation unit 3, and the identification unit 4.

The endoscope 20 transmits, to the surgery assistance apparatus 1 connected to the endoscope 20, a human-body internal image in which the inside of a human body is captured. For example, the endoscope 20 includes an insertion unit that is inserted into the human body, an image-capturing unit that is provided on the distal end-side of the insertion unit, an operation unit for controlling bending of the insertion unit, the capturing of images by the image-capturing unit, etc., and a connection unit that connects the endoscope 20 and the surgery assistance apparatus 1. In addition to the image-capturing unit, the endoscope 20 also includes an illumination unit, a nozzle (nozzles) used for feeding air and water and for suction, a forceps port, and the like on the distal end-side of the insertion unit.

The output device 21 acquires, from the output information generation unit 22, output information converted into formats that can be output, and outputs images, sound, etc., generated on the basis of the output information. The output device 21, for example, includes an image display device utilizing liquid crystals, organic electroluminescence (EL), or a cathode ray tube (CRT), and further includes a sound output device such as a speaker, and the like. Note that the output device 21 may also be a printing device such as a printer.

The feature amount calculation unit 2 acquires a plurality of human-body internal images captured in time series by the endoscope 20, and extracts a feature amount of a target part image corresponding to a target part from the human-body internal images. Furthermore, the feature amount calculation unit 2 includes a feature extraction unit 23, a detection result calculation unit 24, and a heatmap calculation unit 25 that extract feature amounts.

The feature extraction unit 23 extracts, from a human-body internal image, feature extraction information (feature amount f; feature vector) indicating features of a target part image. Specifically, local binary patterns (LBP) is one method for extracting local features of an image, and the extraction method is disclosed for example in the following document: "T. Ojala, M. Pietikainen, and D. Harwood, 'Performance evaluation of texture measures with classification based on Lullback discrimination of distributions,' in the Proceedings of IEEE International Conference on Pattern Recognition, 1994."

Figure 3:
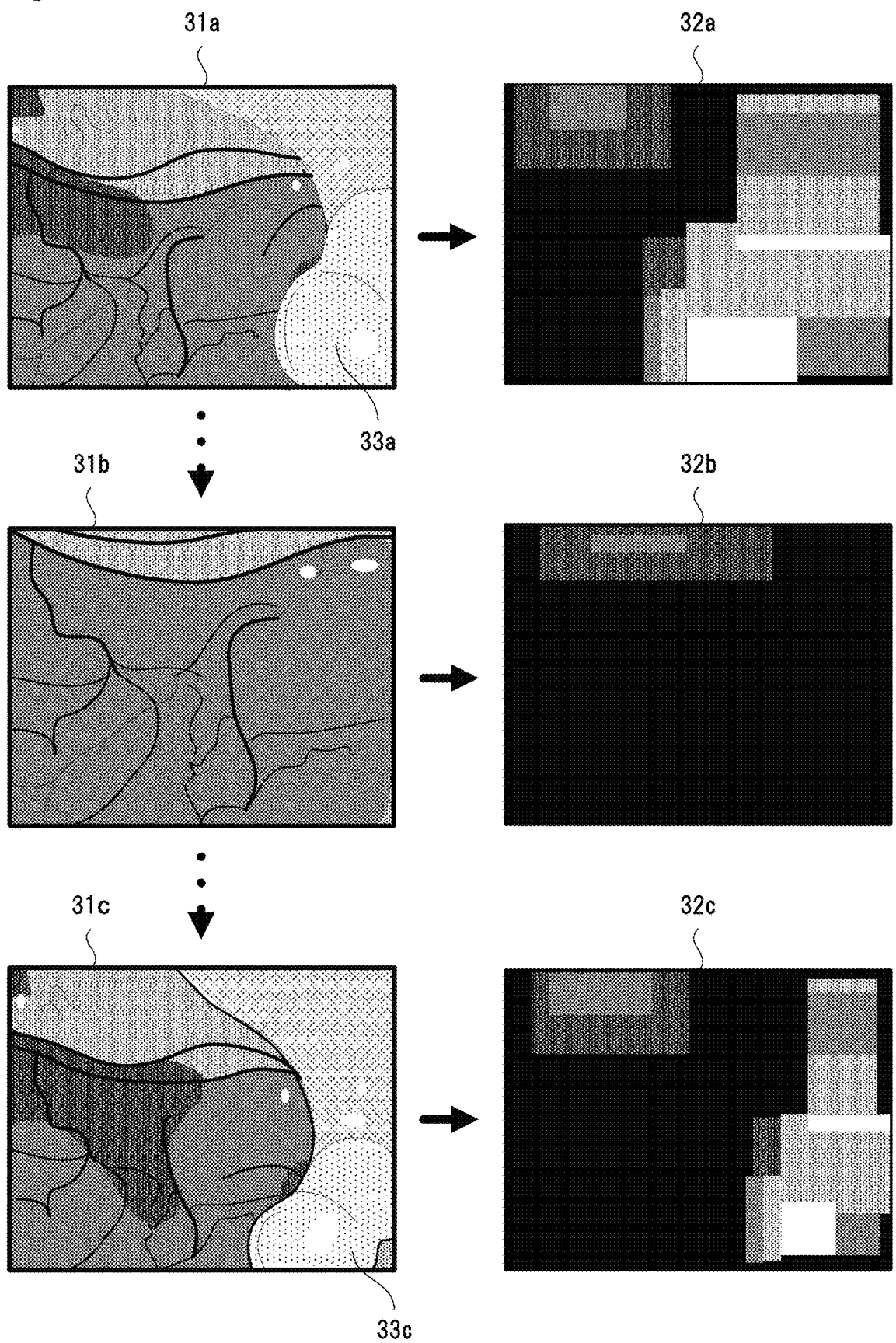
FIG. 3 is a diagram illustrating one example of human-body internal images and images indicating feature amounts.

FIG. 3 is a diagram illustrating one example of human-body internal images and images indicating feature amounts. Human-body internal images 31 (31a, 31b, and 31c) illustrated in FIG. 3 are images in which the inside of a colon is captured in time series, and target part images 33 (33a and 33c) illustrated in FIG. 3 are images in which a tumor is captured. Note that, in FIG. 3, while the target part images 33a and 33c are captured in the human-body internal images 31a and 31c, no target part image is captured in the human-body internal image 31b because the target part moved out of the frame.

In FIG. 3, the feature extraction unit 23 acquires the plurality of human-body internal images that have been captured in time series, in the order of 31a, 31b, and 31c. Note that the human-body internal images may be acquired continuously in the order in which human-body internal images in a moving image are captured.

Next, for each of the acquired human-body internal images 31, the feature extraction unit 23 performs extraction of feature extraction information of a target part image 33 corresponding to the target part. In FIG. 3, images 32 (32a, 32b, and 32c) are illustrated as images indicating the feature extraction information extracted from the human-body internal images 31 (31a, 31b, and 31c). Note that, in the images 32 in FIG. 3, features of the target part are indicated by regions that are white or of a similar color, and the rest is indicated by black regions.

The detection result calculation unit 24 calculates detection result information (feature amounts r; feature vectors) using the feature extraction information (feature amount f, feature vector) extracted from each of the human-body internal images 31. Specifically, the detection result calculation unit 24 applies processing, such as sliding window, for detecting a target part image 33 to each of the images 32 corresponding to the feature extraction information, and calculates the detection result information for each of the human-body internal images 31.

Figure 4:
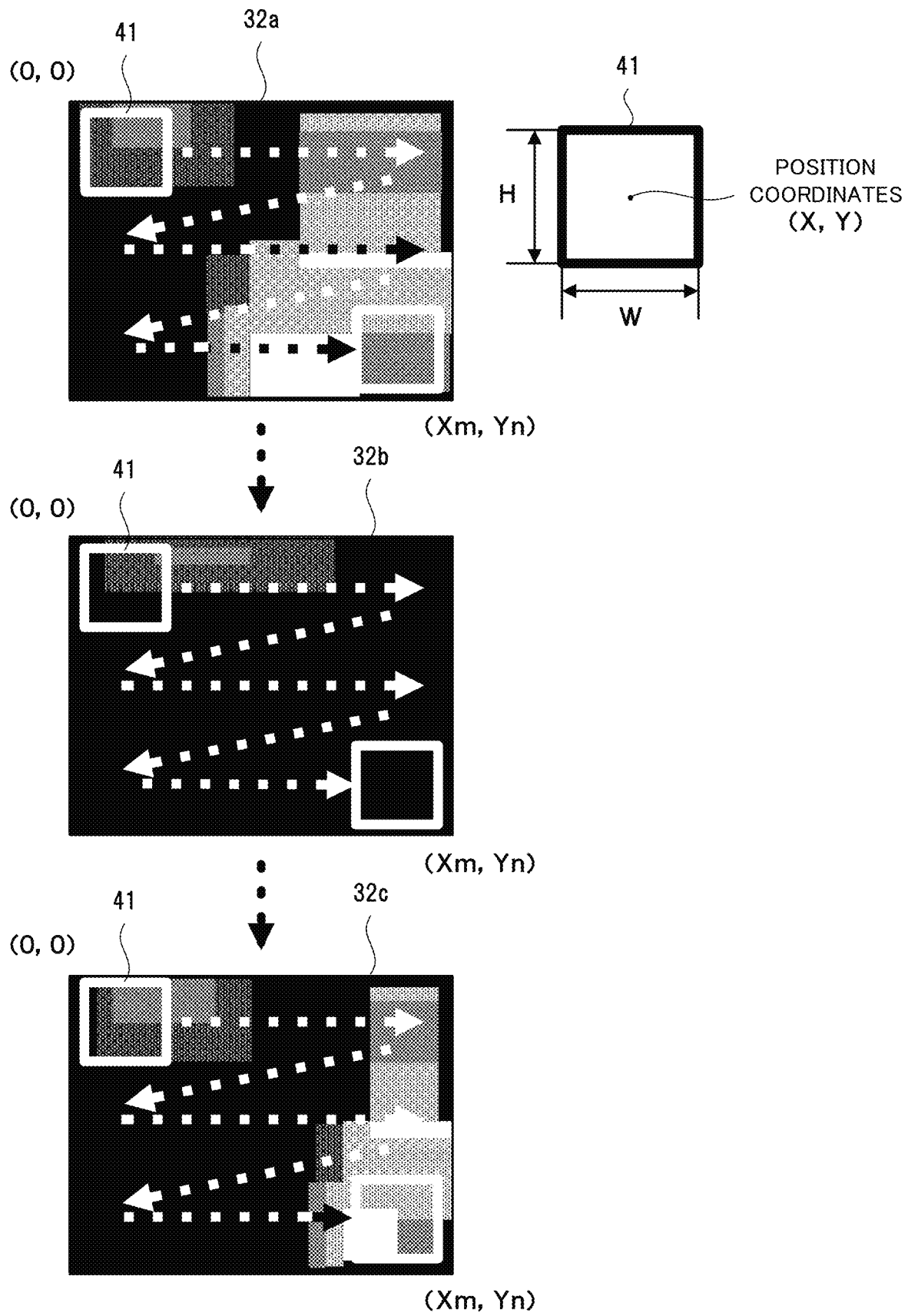
FIG. 4 is a diagram for describing the calculation of detection result information.

FIGS. 4 and 5 are diagrams for describing the calculation of the detection result information. With respect to the images 32 corresponding to the feature extraction information, the detection result calculation unit 24 shifts a window 41 (window region) in the direction of the white arrow illustrated in FIG. 4 (in a predetermined order), and calculates the detection result information each time the window 41 is shifted (each time the window 41 is moved by a predetermined distance), for example. In addition, the detection result calculation unit 24 changes the size of the window 41, uses the window 41' having a different size and shifts the window 41' in the predetermined order, and calculates the detection result information each time the window 41' is shifted. Note that the predetermined order is not limited to that in the direction (horizontal direction) of the white arrow illustrated in FIG. 4.

The detection result information includes, for example, region information indicating the position and size of a detection target part and confidence information indicating the probability of the region of the detection target part corresponding to the target part. The region information and the confidence information are calculated using features inside the windows 41 and 41' (in the following, the window 41' is also referred to as the window 41). The region information, for example, includes position information indicating the position of a rectangle circumscribing the target part, and size information indicating the size of the circumscribing rectangle.

If the images 32 are regarded as two-dimensional coordinate systems, position information indicating a position of the window 41 can be indicated by coordinates inside the window 41. Center coordinates (X, Y) as illustrated in FIG. 4 are one example of coordinates inside the window 41. If the images 32 are regarded as two-dimensional coordinate systems, size information indicating the size of the window 41 can be indicated by the width (W) and height (H) of the window 41 as illustrated in FIG. 4.

Similarly to the region information of the window 41, the region information of the detection result information can be indicated by the center coordinates (Xr, Yr) of the rectangle 42 circumscribing the target part, and size information indicating the size of the rectangle 42 (the width (Wr) and height (Hr) of the rectangle), as illustrated in FIG. 5. Note that the center coordinates of the rectangle 42 circumscribing the target part may be indicated by the relative position to the window 41, i.e., (Xr'=Xr−X, Yr'=Yr−Y). The confidence information is information indicating the probability (conf) of the region of the detection target part corresponding to the target part, which is calculated using the features inside the window 41.

Note that the detection result information may, for example, be expressed in a form such as: feature vector r=(Xr', Yr', Wr, Hr, conf). Furthermore, the region information of the detection result information need not have a rectangular shape. The shape may be circular, elliptical, or the like, for example.

The heatmap calculation unit 25 calculates heatmap information (feature amount h; feature vector) using the feature extraction information (feature amount f; feature vector) extracted from each of the human-body internal images 31. Specifically, the heatmap calculation unit 25 calculates the heatmap information by applying a semantic segmentation technique, for example, to the images 32 corresponding to the feature extraction information.

Figure 6:
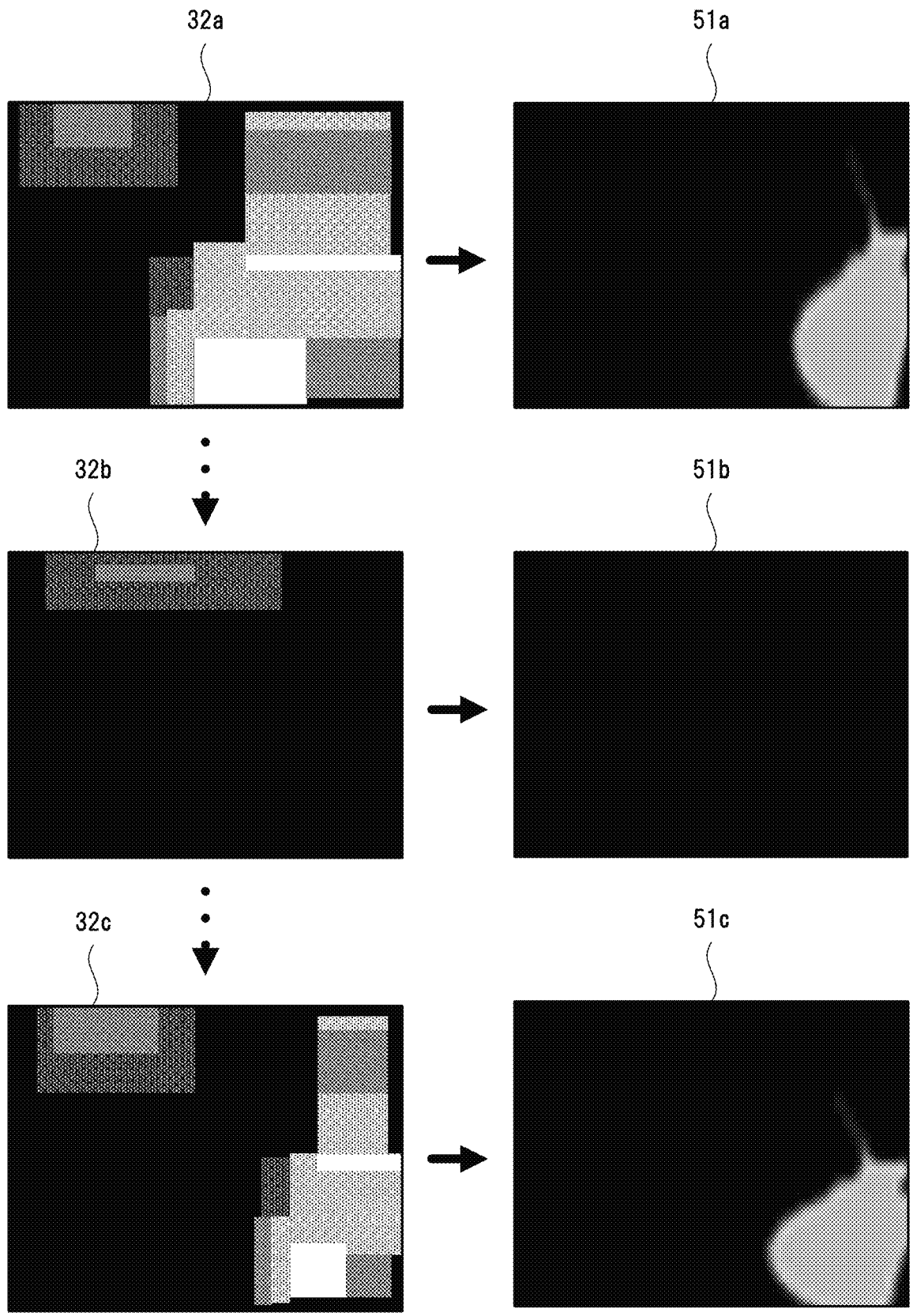
FIG. 6 is a diagram for describing the calculation of heatmap information.

FIG. 6 is a diagram for describing the calculation of the heatmap information. The heatmap calculation unit 25 applies semantic segmentation to the images 32 corresponding to the feature extraction information, and uses different values to express coordinates corresponding to the target part images 33 and coordinates outside the target part images 33. That is, the heatmap calculation unit 25 calculates images 51 (51a, 51b, and 51c) for indicating the heatmap information. Note that, in the images 51 in FIG. 6, the target part is indicated by white regions, and the outside of the target part is indicated by black regions. Note that the coordinates may be expressed using pixels.

Furthermore, the feature extraction unit 23 may calculate feature extraction information (feature amount f': feature vector) and detection result information (r) for each window 41. In addition, the heatmap calculation unit 25 may calculate heatmap information (feature amount h'; feature vector) for each window 41.

Note that the feature amount calculation unit 2 stores the human-body internal images 31 and the above-described feature amounts f, r, and h in an associated state. FIG. 7 is a diagram illustrating one example of a data structure of feature amounts. In FIG. 7, in information 61a indicating feature amounts, feature extraction information (feature amount fa), detection result information (feature amounts r1a, r2a, r3a, and r4a), and heatmap information (feature amount ha) that correspond to the human-body internal image 31a are associated with one another. In information 61b, feature extraction information (feature amount fb), detection result information (feature amounts r1b, r2b, r3b, and r4b), and heatmap information (feature amount hb) that correspond to the human-body internal image 31b are associated with one another. In information 61c, feature extraction information (feature amount fc), detection result information (feature amounts r1c, r2c, r3c, and r4c), and heatmap information (feature amount hc) that correspond to the human-body internal image 31c are associated with one another.

The similarity degree calculation unit 3 calculates a similarity degree using the feature extraction information (feature amount f), the detection result information (feature information r), and the heatmap information (feature amount h) in different human-body internal images 31. Specifically, in the calculation of a similarity degree between human-body internal images 31, a distance between feature vectors (similarity degree) is calculated using feature vectors of the feature extraction information (feature amount f), feature vectors of the detection result information (feature information r), and/or feature vectors of the heatmap information (feature amount h). Alternatively, the similarity degree may be expressed using linear combinations. The similarity degree calculation unit 3 calculates the similarity degree according to the methods described in (1) to (5).

(1) The similarity degree calculation unit 3 calculates a similarity degree of the detection result information (r), a similarity degree of the feature extraction information (f), or a similarity degree of the heatmap information (h).

(2) The similarity degree calculation unit 3 calculates a similarity degree of the position information (X, Y) included in the region information of the detection result information in each window, a similarity degree of the size information (W, H) included in the region information, a similarity degree of the confidence information (conf), a similarity degree of the feature extraction information (f'), or a similarity degree of the heatmap information (h').

(3) The similarity degree calculation unit 3 combines two or more out of the degrees of similarity indicated in (1) and (2), and sets the total sum of the degrees of similarity as a similarity degree. That is, the total sum of two or more out of the similarity degree of the detection result information (r), the similarity degree of the feature extraction information (f), the similarity degree of the heatmap information (h), the similarity degree of the position information (X, Y) included in the region information, the similarity degree of the size information (W, H) included in the region information, the similarity degree of the confidence information (conf), the similarity degree of the feature extraction information (f'), and the similarity degree of the heatmap information (h') is set as a similarity degree.

(4) The similarity degree calculation unit 3 calculates the similarity degree of the confidence information (conf), and if the calculated similarity degree is greater than or equal to a predetermined confidence value that is set in advance, calculates a similarity degree of feature amounts between the different human-body internal images 31 (one or more of the degrees of similarity indicated in (1) and (2) described above). The predetermined confidence value is a determination value calculated through experimentation, simulation, machine learning, etc., and is stored in a storage unit provided in the surgery assistance apparatus or outside the surgery assistance apparatus. Alternatively, the maximum value of confidence information calculated from a plurality of human-body internal images 31 acquired in the past may be set as the predetermined confidence value. By adopting such a configuration, the calculation of a similarity degree becomes unnecessary in a case where the same target part image 33 is continuously captured in human-body internal images 31.

(5) The similarity degree calculation unit 3 calculates the similarity degree of the confidence information (conf), and if the calculated similarity degree is greater than or equal to the predetermined confidence value, calculates the similarity degree of the region information (X, Y, W, H). Next, the similarity degree calculation unit 3 calculates the similarity degree of the feature extraction information (f) if the similarity degree of the region information is greater than or equal to a predetermined region value. Then, the similarity degree calculation unit 3 calculates the similarity degree of the heatmap information (h) if the similarity degree of the feature extraction information is greater than or equal to a predetermined feature extraction value.

Note that each of the predetermined region value and the predetermined feature extraction value is a determination value calculated through experimentation, simulation, machine learning, etc., and is stored in the storage unit provided in the surgery assistance apparatus or outside the surgery assistance apparatus. By adopting such a configuration, the calculation of a similarity degree becomes unnecessary in a case where the same target part image 33 is continuously captured in human-body internal images 31, and the accuracy of degrees of similarity between human-body internal images 31 can be improved.

Furthermore, in the calculation of the similarity degree of the region information in (5), the similarity degree may be calculated using either the position information (X, Y) or the size information (W, H) in the region information.

The identification unit 4 identifies a target part image in each of the different human-body internal images 31 if the similarity degree is greater than or equal to a predetermined value. Specifically, if the similarity degree calculated according to one of (1) to (5) is greater than or equal to the predetermined value, the identification unit 4 associates the target part images 33 in the human-body internal images 31 with one another and stores the target part images 33 in the storage unit. The identification unit 4 performs the identification according to the methods indicated in (1') to (5').

(1') The identification unit 4 identifies the target part images 33 if the similarity degree of the detection result information (r) is greater than or equal to a predetermined detection result value, the similarity degree of the heatmap information (h) is greater than or equal to a predetermined heatmap value, or the similarity degree of the feature extraction information (f) is greater than or equal to the predetermined feature extraction value. The predetermined heatmap value is a determination value calculated through experimentation, simulation, machine learning, etc., and is stored in the storage unit provided in the surgery assistance apparatus 1 or outside the surgery assistance apparatus 1.

(2') The identification unit 4 identifies the target part images 33 if the similarity degree of the position information (X, Y) included in the region information, the similarity degree of the size information (W, H) included in the region information, the similarity degree of the confidence information (conf), the similarity degree of the feature extraction information (f'), and the similarity degree of the heatmap information (h') are all greater than or equal to a predetermined value set for each similarity degree. Alternatively, the identification unit 4 may identify the target part images 33 if any of the degrees of similarity is greater than or equal to the predetermined value.

(3') The identification unit 4 sets the total sum of two or more out of the degrees of similarity indicated in (1) and (2) as the similarity degree, and identifies the target part images 33 if the similarity degree is greater than or equal to a predetermined value that is set for each combination.

(4') The identification unit 4 carries out the identification indicated in (1'), (2'), or (3') if the similarity degree of the confidence information (conf) is greater than or equal to the predetermined confidence value.

(5') The identification unit 4 identifies that the target part images 33 in the different human-body internal images 31 are the same if the similarity degree of the heatmap information (h), which is indicated in (5), is greater than or equal to the predetermined heatmap value.

By adopting such configurations, the target part image 33c captured in the latest human-body internal image 31c and the target part image 33a in the human-body internal image 31a captured in the past can be associated with one another even if the human-body internal image 31b, in which a target part image is not captured, is present between the human-body internal image 31c and the human-body internal image 31a, that is, even if the observer loses track of the target part image 33, for example.

The output information generation unit 22 generates output information indicating that target part images 33 have been identified if target part images 33 are identified during surgery, and transmits the generated output information to the output device 21. The output device 21 acquires the output information, and then outputs, on the basis of the output information, at least one of a screen and sound indicating that target part images 33 have been identified.

Figure 8:
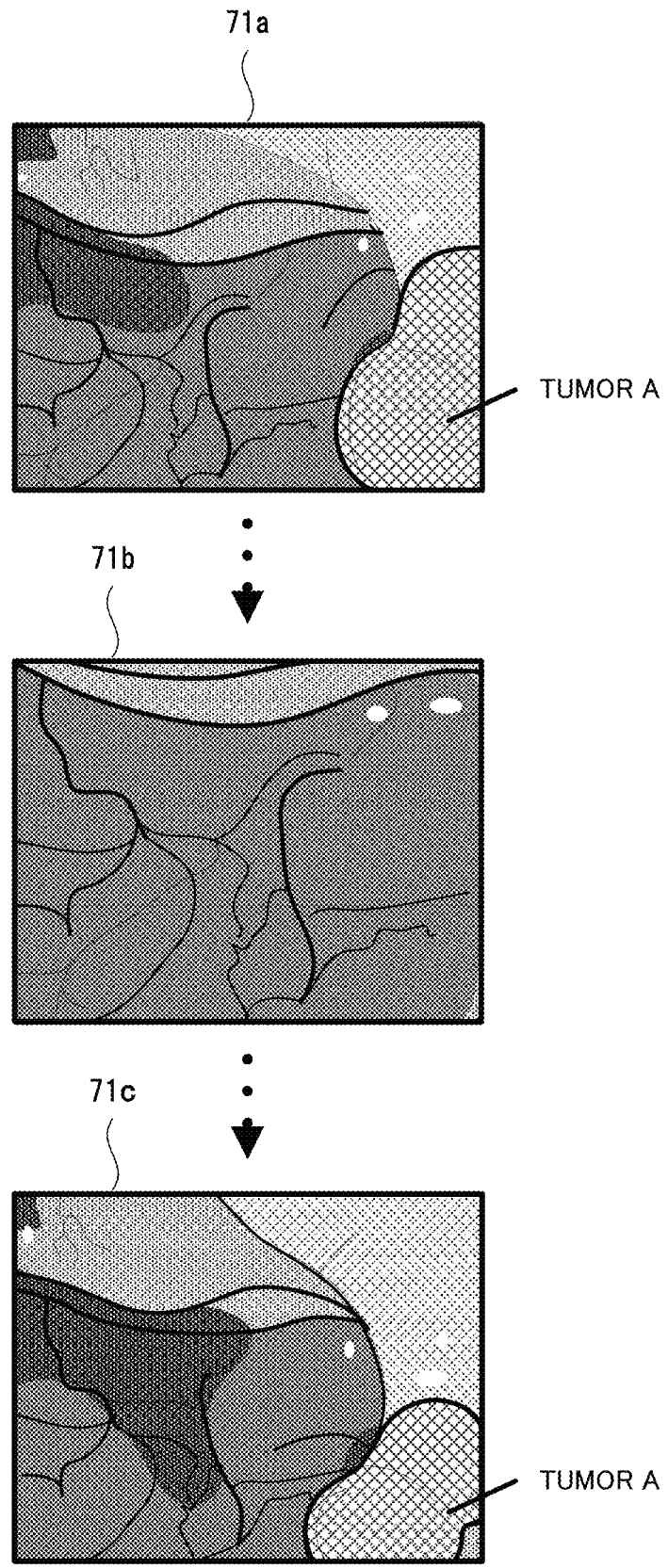
FIG. 8 is a diagram illustrating one example of display in which target part images are identified.

FIG. 8 is a diagram illustrating one example of display in which target part images are identified. In FIG. 8, coloring, etc., is applied to the portions of the identified target part images 33 in the human-body internal images 31a and 31c, and indicators that the identified target part images 33 correspond to the same tumor are also displayed. Note that no indicator regarding identification is displayed for the human-body internal image 31b because the human-body internal image 31b does not include an identified target part image. In FIG. 8, the target part images 33 are colored (the shaded areas), and indicators that the target part images 33 correspond to a "tumor A" are displayed. Note that the display method is not limited to that illustrated in FIG. 8.

[Apparatus Operations]

Figure 9:
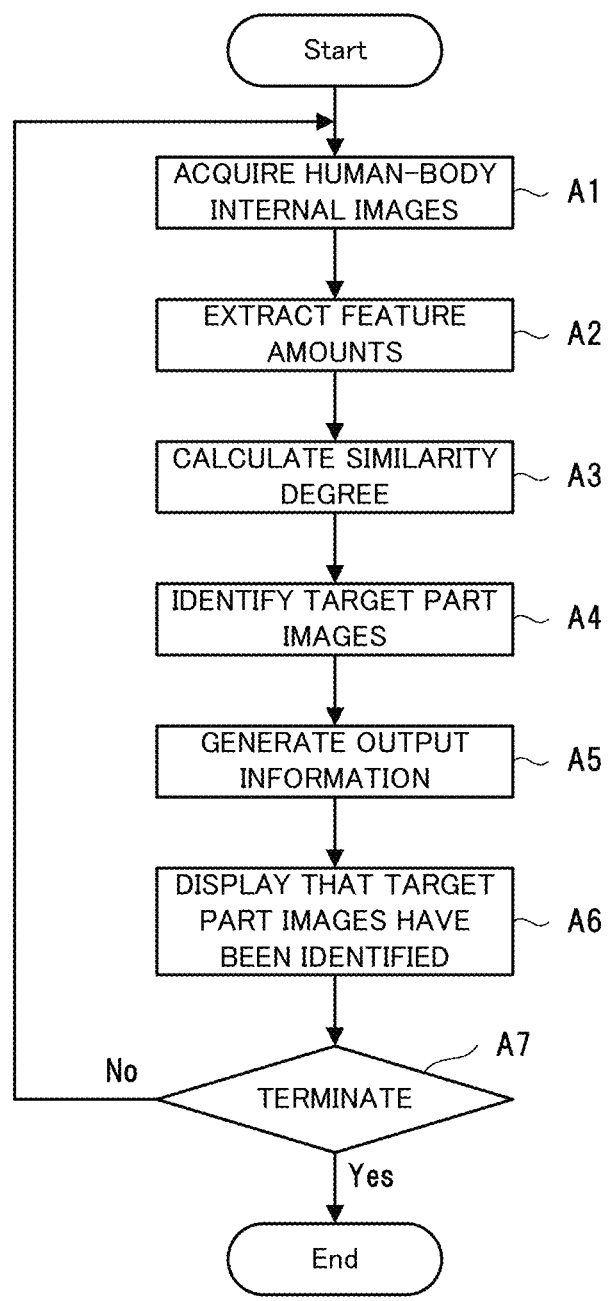
FIG. 9 is a diagram illustrating one example of the operations of the surgery assistance apparatus.

Next, the operations of the surgery assistance apparatus in the example embodiment of the present invention will be described with reference to FIG. 9. FIG. 9 is a diagram illustrating one example of the operations of the surgery assistance apparatus. FIGS. 2 to 8 will be referred to as needed in the following description. Furthermore, in the present example embodiment, a surgery assistance method is implemented by causing the surgery assistance apparatus to operate. Accordingly, the following description of the operations of the surgery assistance apparatus is substituted for the description of the surgery assistance method in the present example embodiment.

In step A1, the feature amount calculation unit 2 acquires human-body internal images 31 that have been captured in time series by the endoscope 20. Next, in step A2, the feature amount calculation unit 2 calculates feature amounts of target part images 33 corresponding to a target part from the human-body internal images 31 captured using the endoscope 20. See FIG. 3.

Specifically, the feature amount calculation unit 2 (feature extraction unit 23) extracts, from the human-body internal images 31, feature extraction information (feature amounts f; feature vectors) indicating features of the target part images 33. Next, the feature amount calculation unit 2 (detection result calculation unit 24) calculates detection result information (feature amounts r; feature vectors) using the feature extraction information (feature amount f; feature vector) extracted from each of the human-body internal images 31. For example, processing, such as sliding window, for detecting a target part image 33 is applied to images 32 corresponding to the feature extraction information, and the detection result information is calculated for each of the human-body internal images 31. See FIGS. 4 and 5.

Alternatively, the feature amount calculation unit 2 (heatmap calculation unit 25) calculates heatmap information (feature amount h; feature vector) using the feature extraction information (feature amount f; feature vector) extracted from each of the human-body internal images 31. The heatmap information is calculated by applying semantic segmentation to the images 32 corresponding to the feature extraction information, for example. See FIG. 6.

Note that the feature amount calculation unit 2 stores the human-body internal images 31 and the above-described feature amounts f, r, and h in an associated state. See FIG. 7.

In step A3, the similarity degree calculation unit 3 calculates a similarity degree using the feature extraction information (feature amount f), the detection result information (feature information r), and/or the heatmap information (feature amount h) in the latest human-body internal image 31 and a human-body internal image 31 captured before the latest human-body internal image 31. Specifically, in the calculation of the similarity degree between the human-body internal images 31, a distance between feature vectors (similarity degree) is calculated using feature vectors of the feature extraction information (feature amount f), feature vectors of the detection result information (feature information r), and/or feature vectors of the heatmap information (feature amount h). Alternatively, the similarity degree may be expressed using linear combinations. The similarity degree calculation unit 3 calculates the similarity degree according to the methods described in (1) to (5).

For example, the similarity degree calculation unit 3 calculates a similarity degree between the latest human-body internal image 31c and the human-body internal image 31a or 31b captured before the latest human-body internal image 31c.

In step A4, the identification unit 4 identifies the target part image 33 in the latest human-body internal image 31 and the target part image 33 in the human-body internal image 31 captured before the latest human-body internal image 31 if the similarity degree is greater than or equal to a predetermined value. Specifically, if the similarity degree calculated according to one of (1) to (5) is greater than or equal to the predetermined value, the identification unit 4 associates the target part images 33 in the human-body internal images 31 with one another and stores the target part images 33 in the storage unit. The identification unit 4 performs the identification according to the methods indicated in (1') to (5').

In step A5, the output information generation unit 22 generates output information indicating that target part images 33 have been identified if target part images 33 are identified during surgery, and transmits the generated output information to the output device 21.

In step A6, the output device 21 acquires the output information, and then outputs, on the basis of the output information, at least one of a screen and sound indicating that target part images 33 have been identified. See FIG. 8.

In step A7, the surgery assistance apparatus 1 terminates the identification processing illustrated in steps A1 to A7 if an instruction to terminate the identification processing is acquired (Yes). The surgery assistance apparatus 1 moves on to the processing in step A1 if the identification processing illustrated in steps A1 to A7 is to continue (No).

[Effects of Example Embodiment]

As described above, according to the present example embodiment, target part images 33 in different human-body internal images 31 captured using an endoscope 20 are identified if a similarity degree of feature amounts of the different human-body internal images 31 is greater than or equal to a predetermined value. Thus, because target part images 33 can be identified, cases where a target part is overlooked can be reduced, regardless of the observer's skill and the like, and thus the accuracy of surgery can be improved.

Cases where the observer loses track of a target part image that is captured using an endoscope can be reduced because a target part image can be identified even if the target part image moves out of the frame or changes as the endoscope is inserted and extracted, for example. Accordingly, the accuracy of endoscopic surgery can be improved.

Also, cases where the observer loses track of a target part image can be reduced because a target part image can be identified even if the target part is frequently concealed by parts of the human body other than the target part (for example, concealment of the target by intestinal folds, intestinal mucus, etc.) or by water ejected from the endoscope, etc. Accordingly, the accuracy of endoscopic surgery can be improved.

Furthermore, cases where the observer loses track of a target part image can be reduced because a target part image can be identified even in the case of non-rigid objects (objects without definite shapes) such as internal parts of the human body and the target part. Accordingly, the accuracy of endoscopic surgery can be improved.

[Program]

It suffices for the program in the example embodiment of the present invention to be a program that causes a computer to carry out steps A1 to A7 illustrated in FIG. 9. By installing this program on a computer and executing the program, the surgery assistance apparatus and the surgery assistance method in the present example embodiment can be realized. In this case, the processor of the computer functions and performs processing as the feature amount calculation unit 2, the similarity degree calculation unit 3, the identification unit 4, and the output information generation unit 22.

Also, the program in the present example embodiment may be executed by a computer system formed from a plurality of computers. In this case, the computers may each function as one of the feature amount calculation unit 2, the similarity degree calculation unit 3, the identification unit 4, and the output information generation unit 22 for example.

[Physical Configuration]

Figure 10:
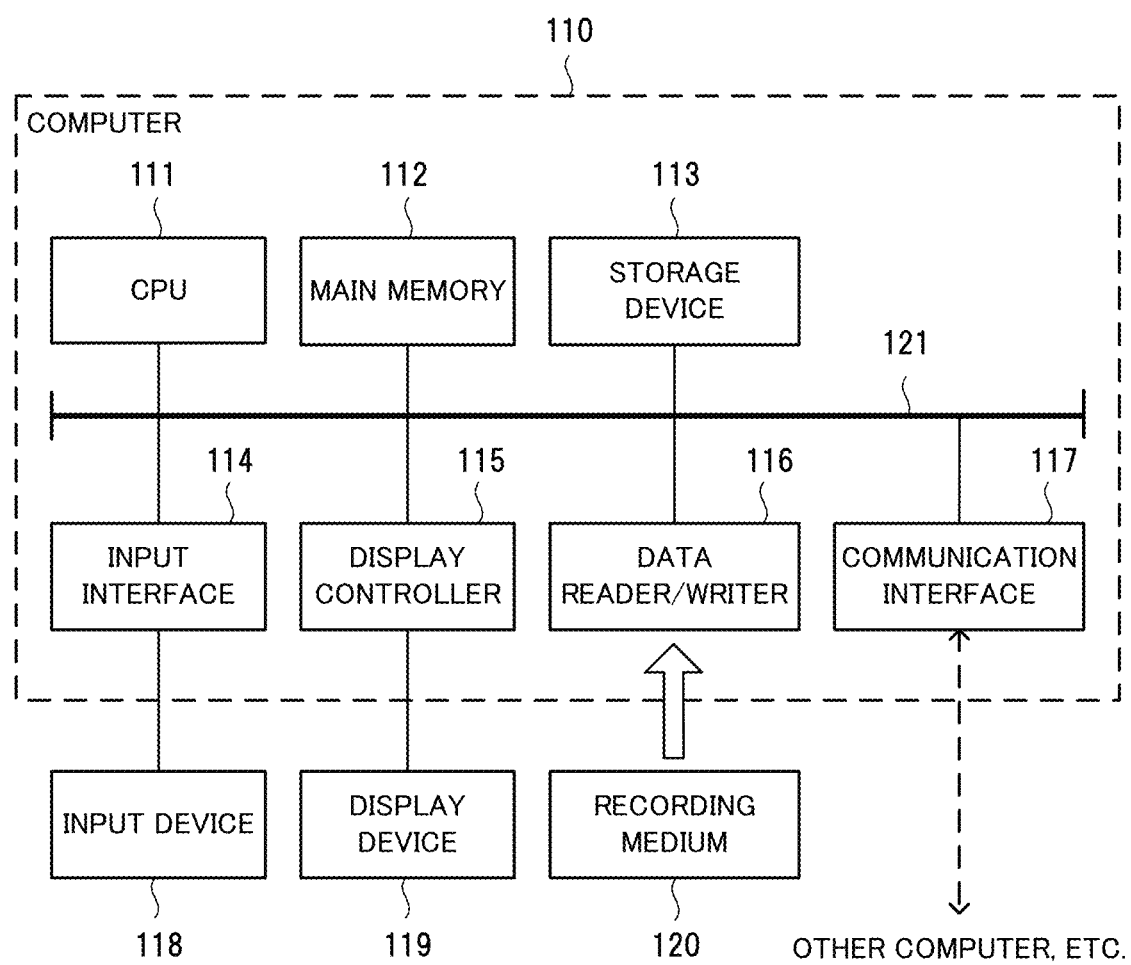
FIG. 10 is a diagram illustrating one example of a computer realizing the surgery assistance apparatus.

Here, a computer that realizes the surgery assistance apparatus by executing the program in the example embodiment will be described with reference to FIG. 10. FIG. 10 is a diagram illustrating one example of a computer realizing the surgery assistance apparatus.

As illustrated in FIG. 10, a computer 110 includes a CPU 111, a main memory 112, a storage device 113, an input interface 114, a display controller 115, a data reader/writer 116, and a communication interface 117. These components are connected via a bus 121 so as to be capable of performing data communication with one another. Note that the computer 110 may include a graphics processing unit (GPU) or a field-programmable gate array (FPGA) in addition to the CPU 111 or in place of the CPU 111.

The CPU 111 loads the program (codes) in the present example embodiment, which is stored in the storage device 113, onto the main memory 112, and performs various computations by executing these codes in a predetermined order. The main memory 112 is typically a volatile storage device such as a dynamic random access memory (DRAM). Furthermore, the program in the present example embodiment is provided in a state such that the program is stored in a computer readable recording medium 120. Note that the program in the present example embodiment may also be a program that is distributed on the Internet, to which the computer 110 is connected via the communication interface 117.

In addition, specific examples of the storage device 113 include semiconductor storage devices such as a flash memory, in addition to hard disk drives. The input interface 114 mediates data transmission between the CPU 111 and input equipment 118 such as a keyboard and a mouse. The display controller 115 is connected to a display device 119, and controls the display performed by the display device 119.

The data reader/writer 116 mediates data transmission between the CPU 111 and the recording medium 120, and executes the reading of the program from the recording medium 120 and the writing of results of processing in the computer 110 to the recording medium 120. The communication interface 117 mediates data transmission between the CPU 111 and other computers.

Furthermore, specific examples of the recording medium 120 include a general-purpose semiconductor storage device such as a CompactFlash (registered trademark, CF) card or a Secure Digital (SD) card, a magnetic recording medium such as a flexible disk, and an optical recording medium such as a compact disk read-only memory (CD-ROM).

[Supplementary Note]

In relation to the above example embodiment, the following Supplementary notes are further disclosed. While apart of or the entirety of the above-described example embodiment can be expressed by (Supplementary note 1) to (Supplementary note 18) described in the following, the present invention is not limited to the following description.

(Supplementary Note 1)

A surgery assistance apparatus including:
    a feature amount calculation unit configured to calculate, from a human-body internal image captured using an endoscope, a feature amount of a target part image corresponding to a target part;

a similarity degree calculation unit configured to calculate a similarity degree of the feature amount between different ones of the human-body internal images; and an identification unit configured to identify the target part image in each of the different human-body internal images if the similarity degree is greater than or equal to a predetermined value.

(Supplementary Note 2)

The surgery assistance apparatus according to Supplementary note 1, wherein the feature amount includes feature extraction information indicating features of the target part image extracted from the human-body internal image, region information indicating the position and size of a window region with which a part or an entirety of an image corresponding to the target part is detected from the feature extraction information, confidence information indicating the probability of the image in the window region being an image corresponding to the target part, heatmap information calculated using the feature extraction information, or information that is a combination of two or more out of the feature extraction information, region information, confidence information, and heatmap information.

(Supplementary Note 3)

The surgery assistance apparatus according to Supplementary note 2, wherein the similarity degree calculation unit calculates the similarity degree of the feature amount between the different human-body internal images if the confidence information is greater than or equal to a predetermined confidence value.

(Supplementary Note 4)

The surgery assistance apparatus according to Supplementary note 2 or 3, wherein the similarity degree calculation unit calculates the similarity degree of the region information if the similarity degree of the confidence information is greater than or equal to a predetermined confidence value, calculates the similarity degree of the feature extraction information if the similarity degree of the region information is greater than or equal to a predetermined region value, and calculates the similarity degree of the heatmap information if the similarity degree of the feature extraction information is greater than or equal to a predetermined feature extraction value, and the identification unit identifies that the target part images in the different human-body internal images are the same if the similarity degree of the heatmap information is greater than or equal to a predetermined heatmap value.

(Supplementary Note 5)

The surgery assistance apparatus according to any one of Supplementary notes 1 to 4, wherein the target part is a tumor, and the target part image is an image in which the tumor is captured.

(Supplementary Note 6)

The surgery assistance apparatus according to any one of Supplementary notes 1 to 5, further including an output device configured to, if the target part image is identified during surgery, output information indicating that the target part image has been identified to an observer during the surgery.

(Supplementary Note 7)

A surgery assistance method including:

(a) a step of calculating, from a human-body internal image captured using an endoscope, a feature amount of a target part image corresponding to a target part;

(b) a step of calculating a similarity degree of the feature amount between different ones of the human-body internal images; and (c) a step of identifying the target part image in each of the different human-body internal images if the similarity degree is greater than or equal to a predetermined value.

(Supplementary Note 8)

The surgery assistance method according to Supplementary note 7, wherein the feature amount includes feature extraction information indicating features of the target part image extracted from the human-body internal image, region information indicating the position and size of a window region with which a part or an entirety of an image corresponding to the target part is detected from the feature extraction information, confidence information indicating the probability of the image in the window region being an image corresponding to the target part, heatmap information calculated using the feature extraction information, or information that is a combination of two or more out of the feature extraction information, region information, confidence information, and heatmap information.

(Supplementary Note 9)

The surgery assistance method according to Supplementary note 8, wherein in the (b) step, the similarity degree of the feature amount between the different human-body internal images is calculated if the confidence information is greater than or equal to a predetermined confidence value.

(Supplementary Note 10)

The surgery assistance method according to Supplementary note 8 or 9, wherein in the (b) step, the similarity degree of the region information is calculated if the similarity degree of the confidence information is greater than or equal to a predetermined confidence value, the similarity degree of the feature extraction information is calculated if the similarity degree of the region information is greater than or equal to a predetermined region value, and the similarity degree of the heatmap information is calculated if the similarity degree of the feature extraction information is greater than or equal to a predetermined feature extraction value, and in the (c) step, the target part images in the different human-body internal images are identified as being the same if the similarity degree of the heatmap information is greater than or equal to a predetermined heatmap value.

(Supplementary Note 11)

The surgery assistance method according to any one of Supplementary notes 7 to 10, wherein the target part is a tumor, and the target part image is an image in which the tumor is captured.

(Supplementary Note 12)

The surgery assistance method according to any one of Supplementary notes 7 to 11, further including (d) a step of, if the target part image is identified during surgery, outputting information indicating that the target part image has been identified to an observer during the surgery.

(Supplementary Note 13)

A computer readable recording medium that includes recorded thereon a surgery assistance program that causes a computer to carry out:

(a) a step of calculating, from a human-body internal image captured using an endoscope, a feature amount of a target part image corresponding to a target part;

(b) a step of calculating a similarity degree of the feature amount between different ones of the human-body internal images; and (c) a step of identifying the target part image in each of the different human-body internal images if the similarity degree is greater than or equal to a predetermined value.

(Supplementary Note 14)

The computer readable recording medium that includes the surgery assistance program recorded thereon according to Supplementary note 13, wherein the feature amount includes feature extraction information indicating features of the target part image extracted from the human-body internal image, region information indicating the position and size of a window region with which a part or an entirety of an image corresponding to the target part is detected from the feature extraction information, confidence information indicating the probability of the image in the window region being an image corresponding to the target part, heatmap information calculated using the feature extraction information, or information that is a combination of two or more out of the feature extraction information, region information, confidence information, and heatmap information.

(Supplementary Note 15)

The computer readable recording medium that includes the surgery assistance program recorded thereon according to Supplementary note 14, wherein in the (b) step, the similarity degree of the feature amount between the different human-body internal images is calculated if the confidence information is greater than or equal to a predetermined confidence value.

(Supplementary Note 16)

The computer readable recording medium that includes the surgery assistance program recorded thereon according to Supplementary note 14 or 15, wherein in the (b) step, the similarity degree of the region information is calculated if the similarity degree of the confidence information is greater than or equal to a predetermined confidence value, the similarity degree of the feature extraction information is calculated if the similarity degree of the region information is greater than or equal to a predetermined region value, and the similarity degree of the heatmap information is calculated if the similarity degree of the feature extraction information is greater than or equal to a predetermined feature extraction value, and in the (c) step, the target part images in the different human-body internal images are identified as being the same if the similarity degree of the heatmap information is greater than or equal to a predetermined heatmap value.

(Supplementary Note 17)

The computer readable recording medium that includes the surgery assistance program recorded thereon according to any one of Supplementary notes 13 to 16, wherein the target part is a tumor, and the target part image is an image in which the tumor is captured.

(Supplementary Note 18)

The computer readable recording medium that includes the surgery assistance program recorded thereon according to any one of Supplementary notes 13 to 17, wherein the surgery assistance program further causes the computer to carry out (d) a step of, if the target part image is identified during surgery, outputting information indicating that the target part image has been identified to an observer during the surgery.

INDUSTRIAL APPLICABILITY

In such a manner, according to the present invention, the accuracy of endoscopic surgery can be improved by identifying a target part image. The present invention is useful in fields in which endoscopic surgery is necessary.

REFERENCE SIGNS LIST

1 Surgery assistance apparatus
2 Feature amount calculation unit
3 Similarity degree calculation unit
4 Identification unit
20 Endoscope
21 Output device
22 Output information generation unit
23 Feature extraction unit
24 Detection result calculation unit
25 Heatmap calculation unit
110 Computer
111 CPU
112 Main memory
113 Storage device
114 Input interface
115 Display controller
116 Data reader/writer
117 Communication interface
118 Input equipment
119 Display device
120 Recording medium
121 Bus

The invention claimed is:

1. A surgery assistance apparatus comprising: a memory storing instructions; and at least one processor configured to access the at least one memory and execute the instructions to implement:

calculating, from a human-body internal image captured using an endoscope, a feature amount of a target part image corresponding to a target part, the feature amount including feature extraction information, region information, confidence information, and heatmap information, wherein the feature extraction information indicates features of the target part image extracted from the human-body internal image, the region information indicates a position and a size of a window region with which a part or an entirety of an image corresponding to the target part is detected from the feature extraction information, the confidence information indicates the probability of the image in the window region being an image corresponding to the target part, and the heatmap information is calculated using the feature extraction information;

calculating a similarity degree of the confidence information between different human-body internal images, including the human-body image;

calculating, based on determining that the similarity degree of the confidence information is greater than or equal to a predetermined confidence value, at least one of a similarity degree of the feature extraction information between the different human-body internal images, a similarity degree of the region information between the different human-body internal images, and a similarity degree of the heatmap information between the different human-body internal images; and identifying the target part image in each of the different human-body internal images based on determining whether the similarity degree is greater than or equal to a predetermined value.

2. The surgery assistance apparatus according to claim 1, wherein the at least one processor is further configured to execute the instructions to implement:

calculating the similarity degree of the region information based on determining whether the similarity degree of the confidence information is greater than or equal to a predetermined confidence value;

calculating the similarity degree of the feature extraction information based on determining whether the similarity degree of the region information is greater than or equal to a predetermined region value;

calculating the similarity degree of the heatmap information based on determining whether the similarity degree of the feature extraction information is greater than or equal to a predetermined feature extraction value; and identifying that the target part images in the different human-body internal images are the same based on determining whether the similarity degree of the heatmap information is greater than or equal to a predetermined heatmap value.

3. The surgery assistance apparatus according to claim 1, wherein
the target part is a tumor, and the target part image is an image in which the tumor is captured.

4. The surgery assistance apparatus according to claim 1, wherein the at least one processor is further configured to execute the instructions to implement outputting, based on determining whether the target part image is identified during surgery, information indicating that the target part image has been identified to an observer during the surgery.

5. The surgery assistance apparatus according to claim 4, wherein the at least one processor is further configured to execute the instructions to implement outputting the information for supporting decision making by the observer on the surgery for a patient.

6. The surgery assistance apparatus according to claim 1, wherein
the predetermined confidence value is determined by using machine learning.

7. A surgery assistance method comprising:

calculating, from a human-body internal image captured using an endoscope, a feature amount of a target part image corresponding to a target part, the feature amount including feature extraction information, region information, confidence information, and heatmap information, wherein the feature extraction information indicates features of the target part image extracted from the human-body internal image, the region information indicates a position and a size of a window region with which a part or an entirety of an image corresponding to the target part is detected from the feature extraction information, the confidence information indicates the probability of the image in the window region being an image corresponding to the target part, and the heatmap information is calculated using the feature extraction information;

calculating a similarity degree of the confidence information between different human-body internal images, including the human-body image; and calculating, based on determining that the similarity degree of the confidence information is greater than or equal to a predetermined confidence value, at least one of a similarity degree of the feature extraction information between the different human-body internal images, a similarity degree of the region information between the different human-body internal images, and a similarity degree of the heatmap information between the different human-body internal images; and identifying the target part image in each of the different human-body internal images if the similarity degree is greater than or equal to a predetermined value.

8. The surgery assistance method according to claim 7, further comprising:

calculating the similarity degree of the region information based on determining whether the similarity degree of the confidence information is greater than or equal to a predetermined confidence value;

calculating the similarity degree of the feature extraction information based on determining whether the similarity degree of the region information is greater than or equal to a predetermined region value;

calculating the similarity degree of the heatmap information based on determining whether the similarity degree of the feature extraction information is greater than or equal to a predetermined feature extraction value; and identifying that the target part images in the different human-body internal images are the same based on determining whether the similarity degree of the heatmap information is greater than or equal to a predetermined heatmap value.

9. The surgery assistance method according to claim 7, wherein
the target part is a tumor, and the target part image is an image in which the tumor is captured.

10. The surgery assistance method according to claim 7, further comprising
outputting, based on determining whether the target part image is identified during surgery, information indicating that the target part image has been identified to an observer during the surgery using an output device.

11. A non-transitory computer readable recording medium that includes recorded thereon a surgery assistance program that causes a computer to carry out:

calculating, from a human-body internal image captured using an endoscope, a feature amount of a target part image corresponding to a target part, the feature amount including feature extraction information, region information, confidence information, and heatmap information, wherein the feature extraction information indicates features of the target part image extracted from the human-body internal image, the region information indicates a position and a size of a window region with which a part or an entirety of an image corresponding to the target part is detected from the feature extraction information, the confidence information indicates the probability of the image in the window region being an image corresponding to the target part, and the heatmap information is calculated using the feature extraction information;

calculating a similarity degree of the confidence information between different human-body internal images, including the human-body image; and calculating, based on determining that the similarity degree of the confidence information is greater than or equal to a predetermined confidence value, at least one of a similarity degree of the feature extraction information between the different human-body internal images, a similarity degree of the region information between the different human-body internal images, and a similarity degree of the heatmap information between the different human-body internal images.

\* \* \* \* \*